(12) United States Patent
Tedgui et al.

(10) Patent No.: US 8,324,152 B2
(45) Date of Patent: Dec. 4, 2012

(54) COMPOSITION FOR THE TREATMENT OF ATHEROSCLEROSIS

(75) Inventors: Alain Tedgui, Paris (FR); Ziad Mallat, Herbeville (FR)

(73) Assignee: Institute National de la Sante et de la Recherche Medicale (INSERM), Paris (FR)

( * ) Notice: Subject to any disclaimer, the term of this patent is extended or adjusted under 35 U.S.C. 154(b) by 631 days.

(21) Appl. No.: 11/813,071

(22) PCT Filed: Jan. 4, 2006

(86) PCT No.: PCT/IB2006/000291
§ 371 (c)(1),
(2), (4) Date: Mar. 3, 2008

(87) PCT Pub. No.: WO2006/072888
PCT Pub. Date: Jul. 13, 2006

(65) Prior Publication Data
US 2009/0215697 A1  Aug. 27, 2009

Related U.S. Application Data

(60) Provisional application No. 60/667,431, filed on Apr. 1, 2005.

(30) Foreign Application Priority Data

Jan. 4, 2005 (EP) ..................................... 05290008

(51) Int. Cl.
*A61P 9/10* (2006.01)
*A61K 38/10* (2006.01)
*C07K 14/775* (2006.01)
*C07K 7/08* (2006.01)

(52) U.S. Cl. ........ 514/1.9; 514/21.4; 514/824; 530/326; 530/359; 530/830

(58) Field of Classification Search ........................ None
See application file for complete search history.

(56) References Cited

U.S. PATENT DOCUMENTS

| 5,049,387 | A | 9/1991 | Amkraut |
| 5,730,969 | A | 3/1998 | Hora et al. |
| 7,704,499 | B2 * | 4/2010 | Nilsson et al. ............. 424/130.1 |
| 2003/0105003 | A1 * | 6/2003 | Nilsson et al. .................. 514/12 |
| 2004/0028727 | A1 | 2/2004 | Glenn et al. |
| 2004/0047870 | A1 | 3/2004 | Harats et al. |

FOREIGN PATENT DOCUMENTS

| JP | 2004529143 A | 9/2004 |
| WO | WO-98/20734 | 5/1998 |
| WO | WO-02/080954 | 10/2002 |

OTHER PUBLICATIONS

Fredrikson et al (2003. Arterioscler Thromb Vasc Biol. 23: 879-884).*
Apostolou et al, 2004. J Exp Med. 199(10): 1401-1408).*
Herbin et al, 2007. Circulation. 116(6): S145.*
Benjamini et al, 1991. Immunology: A Short Course, 2nd edition. P. 40 only. 3 pages as printed.*
Zhou, "Immunomodulation and Vaccination for Atherosclerosis", 2004, pp. 599-612, vol. 4, No. 4, Expert Opinion on Biological Therapy, United Kingdom.
Mallat et al, "Immunomodulation to Combat Atherosclerosis: The Potential Role of Immune Regulatory Cells", 2004, pp. 1387-1393, vol. 4, No. 9, Expert Opinion on Biological Therapy, United Kingdom.
Schiopu et al, "Recombinant Human Antibodies Against Aldehyde-Modified Apolipoprotein B-100 Peptide Sequences Inhibit Atherosclerosis", Oct. 5, 2004, pp. 2047-2052, Circulation Oct. 5, 2004, United States.
Ehrenhofer et al., "The Effects of Continuos and Intermittent Delivery of Antigens of Boophilus Microplus on the Development of Murine Antibodies", Veterinary Parasitology 59 (1995) 263-273.
Japanese Office Action dated May 8, 2012, from corresponding JP application.

* cited by examiner

*Primary Examiner* — Zachary Howard
(74) *Attorney, Agent, or Firm* — Young & Thompson

(57) ABSTRACT

The present invention concern a composition or a patch adapted for the prophylactic or therapeutic treatment by continuous subcutaneous administration of a subject suffering from atherosclerosis, comprising an effective amount of at least one epitope derived from a protein present in the atherosclerotic plaque, whereby administration of said at least one epitope to said subject induces a specific regulatory immune response, preferably a Treg response.

7 Claims, No Drawings

SEQUENCE LISTING

```
<160> NUMBER OF SEQ ID NOS: 40

<210> SEQ ID NO 1
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 1

Phe Leu Asp Thr Val Tyr Gly Asn Cys Ser Thr His Phe Thr Val Lys
1               5                   10                  15

Thr Arg Lys Gly
            20

<210> SEQ ID NO 2
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 2

Pro Gln Cys Ser Thr His Ile Leu Gln Trp Leu Lys Arg Val His Ala
1               5                   10                  15

Asn Pro Leu Leu
            20

<210> SEQ ID NO 3
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 3

Val Ile Ser Ile Pro Arg Leu Gln Ala Glu Ala Arg Ser Glu Ile Leu
1               5                   10                  15

Ala His Trp Ser
            20

<210> SEQ ID NO 4
<211> LENGTH: 20
<212> TYPE: PRT
<213> ORGANISM: Artificial sequence
```

```
<220> FEATURE:
<223> OTHER INFORMATION: peptide derived from apolipoprotein B

<400> SEQUENCE: 4

Lys Leu Val Lys Glu Ala Leu Lys Glu Ser Gln Leu Pro Thr Val Met
1               5                   10                  15

Asp Phe Arg Lys
            20

<210> SEQ ID NO 5
<211> LENGTH: 19
<212> TYPE: PRT
<213> ORGANISM: Artificial sequence
<220> FEATURE:
<223> OTHER INFORMATION: peptide derived from apolipoprotein B

<400> SEQUENCE: 5

Leu Phe Val Thr Gln Ala Glu Gly Ala Lys Gln Thr Glu Ala Thr Met
1               5                   10                  15

Thr Phe Lys

<210> SEQ ID NO 6
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 6

Asp Gly Ser Leu Arg His Lys Phe Leu Asp Ser Asn Ile Lys Phe Ser
1               5                   10                  15

His Val Glu Lys
            20

<210> SEQ ID NO 7
<211> LENGTH: 20
<212> TYPE: PRT
<213> ORGANISM: Artificial
<220> FEATURE:
<223> OTHER INFORMATION: peptide derived from apolipoprotein B

<400> SEQUENCE: 7

Lys Gly Thr Tyr Gly Leu Ser Cys Gln Arg Asp Pro Asn Thr Gly Arg
1               5                   10                  15

Leu Asn Gly Glu
            20

<210> SEQ ID NO 8
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 8

Arg Leu Asn Gly Glu Ser Asn Leu Arg Phe Asn Ser Ser Tyr Leu Gln
1               5                   10                  15

Gly Thr Asn Gln
            20

<210> SEQ ID NO 9
<211> LENGTH: 20
<212> TYPE: PRT
<213> ORGANISM: Artificial sequence
```

```
<220> FEATURE:
<223> OTHER INFORMATION: peptide derived from apolipoprotein B

<400> SEQUENCE: 9

Ser Leu Thr Ser Thr Ser Asp Leu Gln Ser Gly Ile Ile Lys Asn Thr
1               5                   10                  15

Ala Ser Leu Lys
            20

<210> SEQ ID NO 10
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 10

Thr Ala Ser Leu Lys Tyr Glu Asn Tyr Glu Leu Thr Leu Lys Ser Asp
1               5                   10                  15

Thr Asn Gly Lys
            20

<210> SEQ ID NO 11
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 11

Asp Met Thr Ser Phe Lys Gln Asn Ala Leu Leu Arg Ser Glu Tyr Gln
1               5                   10                  15

Ala Asp Tyr Glu
            20

<210> SEQ ID NO 12
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 12

Met Lys Val Lys Ile Ile Arg Thr Ile Asp Gln Met Gln Asn Ser Glu
1               5                   10                  15

Leu Gln Trp Pro
            20

<210> SEQ ID NO 13
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 13

Ile Ala Leu Asp Asp Ala Lys Ile Asn Phe Asn Glu Lys Leu Ser Gln
1               5                   10                  15

Leu Gln Thr Tyr
            20

<210> SEQ ID NO 14
<211> LENGTH: 20
<212> TYPE: PRT
<213> ORGANISM: Artificial sequence
```

```
<220> FEATURE:
<223> OTHER INFORMATION: peptide derived from apolipoprotein B

<400> SEQUENCE: 14

Lys Thr Thr Lys Gln Ser Phe Asp Leu Ser Val Lys Ala Gln Tyr Lys
1               5                   10                  15

Lys Asn Lys His
            20

<210> SEQ ID NO 15
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 15

Glu Glu Glu Met Leu Glu Asn Val Ser Leu Val Cys Pro Lys Asp Ala
1               5                   10                  15

Thr Arg Phe Lys
            20

<210> SEQ ID NO 16
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 16

Gly Ser Thr Ser His His Leu Val Ser Arg Lys Ser Ile Ser Ala Ala
1               5                   10                  15

Leu Glu His Lys
            20

<210> SEQ ID NO 17
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 17

Ile Glu Asn Ile Asp Phe Asn Lys Ser Gly Ser Ser Thr Ala Ser Trp
1               5                   10                  15

Ile Gln Asn Val
            20

<210> SEQ ID NO 18
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 18

Ile Arg Glu Val Thr Gln Arg Leu Asn Gly Glu Ile Gln Ala Leu Glu
1               5                   10                  15

Leu Pro Gln Lys
            20

<210> SEQ ID NO 19
<211> LENGTH: 20
<212> TYPE: PRT
<213> ORGANISM: Artificial sequence
```

```
<220> FEATURE:
<223> OTHER INFORMATION: peptide derived from apolipoprotein B

<400> SEQUENCE: 19

Glu Val Asp Val Leu Thr Lys Tyr Ser Gln Pro Glu Asp Ser Leu Ile
1               5                   10                  15

Pro Phe Phe Glu
            20

<210> SEQ ID NO 20
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 20

His Thr Phe Leu Ile Tyr Ile Thr Glu Leu Leu Lys Lys Leu Gln Ser
1               5                   10                  15

Thr Thr Val Met
            20

<210> SEQ ID NO 21
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 21

Leu Leu Asp Ile Ala Asn Tyr Leu Met Glu Gln Ile Gln Asp Asp Cys
1               5                   10                  15

Thr Gly Asp Glu
            20

<210> SEQ ID NO 22
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 22

Cys Thr Gly Asp Glu Asp Tyr Thr Tyr Lys Ile Lys Arg Val Ile Gly
1               5                   10                  15

Asn Met Gly Gln
            20

<210> SEQ ID NO 23
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 23

Gly Asn Met Gly Gln Thr Met Glu Gln Leu Thr Pro Glu Leu Lys Ser
1               5                   10                  15

Ser Ile Leu Lys
            20

<210> SEQ ID NO 24
<211> LENGTH: 20
<212> TYPE: PRT
<213> ORGANISM: Artificial sequence
```

```
<220> FEATURE:
<223> OTHER INFORMATION: peptide derived from apolipoprotein B

<400> SEQUENCE: 24

Ser Ser Ile Leu Lys Cys Val Gln Ser Thr Lys Pro Ser Leu Met Ile
1               5                   10                  15

Gln Lys Ala Ala
            20

<210> SEQ ID NO 25
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 25

Ile Gln Lys Ala Ala Ile Gln Ala Leu Arg Lys Met Glu Pro Lys Asp
1               5                   10                  15

Lys Asp Gln Glu
            20

<210> SEQ ID NO 26
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 26

Arg Leu Asn Gly Glu Ser Asn Leu Arg Phe Asn Ser Ser Tyr Leu Gln
1               5                   10                  15

Gly Thr Asn Gln
            20

<210> SEQ ID NO 27
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 27

Ser Leu Asn Ser His Gly Leu Glu Leu Asn Ala Asp Ile Leu Gly Thr
1               5                   10                  15

Asp Lys Ile Asn
            20

<210> SEQ ID NO 28
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 28

Trp Ile Gln Asn Val Asp Thr Lys Tyr Gln Ile Arg Ile Gln Ile Gln
1               5                   10                  15

Glu Lys Leu Gln
            20

<210> SEQ ID NO 29
<211> LENGTH: 20
<212> TYPE: PRT
<213> ORGANISM: Artificial sequence
```

```
<220> FEATURE:
<223> OTHER INFORMATION: peptide derived from apolipoprotein B

<400> SEQUENCE: 29

Thr Tyr Ile Ser Asp Trp Trp Thr Leu Ala Ala Lys Asn Leu Thr Asp
1               5                   10                  15

Phe Ala Glu Gln
            20

<210> SEQ ID NO 30
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 30

Glu Ala Thr Leu Gln Arg Ile Tyr Ser Leu Trp Glu His Ser Thr Lys
1               5                   10                  15

Asn His Leu Gln
            20

<210> SEQ ID NO 31
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 31

Ala Leu Leu Val Pro Pro Glu Thr Glu Glu Ala Lys Gln Val Leu Phe
1               5                   10                  15

Leu Asp Thr Val
            20

<210> SEQ ID NO 32
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 32

Ile Glu Ile Gly Leu Glu Gly Lys Gly Phe Glu Pro Thr Leu Glu Ala
1               5                   10                  15

Leu Phe Gly Phe
            20

<210> SEQ ID NO 33
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 33

Ser Gly Ala Ser Met Lys Leu Thr Thr Asn Gly Arg Phe Arg Glu His
1               5                   10                  15

Asn Ala Lys Phe
            20

<210> SEQ ID NO 34
<211> LENGTH: 20
<212> TYPE: PRT
<213> ORGANISM: Artificial sequence
```

```
<220> FEATURE:
<223> OTHER INFORMATION: peptide derived from apolipoprotein B

<400> SEQUENCE: 34

Asn Leu Ile Gly Asp Phe Glu Val Ala Glu Lys Ile Asn Ala Phe Arg
1               5                   10                  15

Ala Lys Val His
            20

<210> SEQ ID NO 35
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 35

Gly His Ser Val Leu Thr Ala Lys Gly Met Ala Leu Phe Gly Glu Gly
1               5                   10                  15

Lys Ala Glu Phe
            20

<210> SEQ ID NO 36
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 36

Phe Lys Ser Ser Val Ile Thr Leu Asn Thr Asn Ala Glu Leu Phe Asn
1               5                   10                  15

Gln Ser Asp Ile
            20

<210> SEQ ID NO 37
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 37

Phe Pro Asp Leu Gly Gln Glu Val Ala Leu Asn Ala Asn Thr Lys Asn
1               5                   10                  15

Gln Lys Ile Arg
            20

<210> SEQ ID NO 38
<211> LENGTH: 20
<212> TYPE: PRT
<213> ORGANISM: Artificial sequence
<220> FEATURE:
<223> OTHER INFORMATION: peptide derived from apolipoprotein B

<400> SEQUENCE: 38

Ala Thr Arg Phe Lys His Leu Arg Lys Tyr Thr Tyr Asn Tyr Gln Ala
1               5                   10                  15

Gln Ser Ser Ser
            20

<210> SEQ ID NO 39
<211> LENGTH: 14
<212> TYPE: PRT
<213> ORGANISM: Artificial sequence
```

```
-continued

<220> FEATURE:
<223> OTHER INFORMATION: peptide derived from apolipoprotein B

<400> SEQUENCE: 39

Gln Glu Val Ala Leu Asn Ala Asn Thr Lys Asn Gln Lys Ile
1               5                   10

<210> SEQ ID NO 40
<211> LENGTH: 17
<212> TYPE: PRT
<213> ORGANISM: Artificial sequence
<220> FEATURE:
<223> OTHER INFORMATION: peptide derived from ovalbumin

<400> SEQUENCE: 40

Ile Ser Gln Ala Val His Ala Ala His Ala Glu Ile Asn Glu Ala Gly
1               5                   10                  15

Arg
```

COMPOSITION FOR THE TREATMENT OF ATHEROSCLEROSIS

This application is a 371 of PCT/IB06/00291, which was filed Jan. 4, 2006, which in turn claims priority to U.S. Provisional Application No. 60/667,431, which was filed Apr. 1, 2005.

The present invention relates to the prevention or treatment of atherosclerosis, in particular to a composition comprising at least one epitope derived from a protein present in the atherosclerotic, which can be administrated to a subject suffering from atherosclerosis and use thereof.

Atherosclerosis is the most common cause of death in western societies and is predicted to become the leading cause of cardiovascular disease in the world within two decades.

Atherosclerosis can be considered to be a form of chronic inflammation resulting from interaction between modified lipoproteins, monocyte-derived macrophages, T cells and the normal cellular elements of the arterial wall. This inflammatory process can ultimately lead to the development of complex lesions or plaques that may protrude into the arterial lumen. Plaque rupture/erosion and thrombosis results in the acute clinical complications of myocardial infarction and stroke (ROSS, *N. Eng. J. Med.*, vol. 340, p: 115-126, 1999; LIBBY, *Nature*, vol: 420, p: 868-74, 2002; VIRMANI et al., *Arterioscler. Thromb. Vasc. Biol.*, vol. 20, p: 1262-1275, 2000).

The disease is initiated by accumulation of lipoproteins particles in the extra-cellular matrix of the vessel. The principal lipid components of lipoprotein particles are cholesterol, triglycerides and phospholipids. Cholesterol is required for normal cellular function and forms an important component of cell membranes. Cholesterol exits in various forms in the circulation and the major component is low-density lipoprotein cholesterol (LDLC, approximately 60% of total serum cholesterol), with about 25% in the form of high-density lipoprotein cholesterol (HDLc) and the remainder circulating in very low-density lipoprotein cholesterol (VLDLc) and other lipoprotein particles. Plasma lipid levels are determined by both genetic and environmental factors such as the LDL receptor locus, apolipoprotein B, genetic polymorphisms, diet, obesity and alcohol intake. Common abnormalities of lipid levels include raised LDLc, a low HDLc and high triglyceride level or a combination of these lipid disturbances.

The common abnormalities of plasma lipid levels described above contribute to the development of atherosclerotic vascular diseases (AVD) which may affect the coronary arteries (causing ischaemic heart disease), the cerebral circulation (causing cerebrovascular disease), the aorta (producing aneurysms that are prone to thrombosis and rupture) and peripheral blood vessels, typically the legs (causing peripheral vascular disease and intermittent claudication).

Ischaemic heart disease (IHD) includes angina (chest pain caused by insufficient blood supply to cardiac muscle) and myocardial infarction (death of cardiac muscle) and cerebrovascular disease includes stroke and transient ischaemic attacks. One in three men and one in four women will die from IHD and the death rate for IHD was 58 per 100,000 in 1990.

HDLc levels are inversely associated with risk of AVD and patterns of lipid abnormalities reflected by an increased ratio of total cholesterol to HDLc, combined with raised fasting triglyceride levels, are a better predictor of risk of IHD than total cholesterol levels alone. A high ratio in combination with increased fasting triglyceride levels is frequently associated with the atherogenic lipoprotein phenotype (ALP), which also includes the presence of increased concentrations of small dense LDL particles. Other cardiovascular risk factors are known to predispose to atherosclerosis, including hypertension, smoking, diabetes, obesity, sedentarity.

Plasma levels of several mediators of inflammation or endothelial dysfunction have been found to predict future cardiovascular events. These biomarkers include, but are not restricted to, hsCRP, IL-6, CD40L, IL-10, IL-18, MMP9, PlGF, circulating microparticles, secretory PLA2, circulating endothelial cells, circulating endothelial progenitor cells.

Atherosclerotic plaques begin as fatty streaks underlying the endothelium of large arteries. Recruitment of macrophages and their subsequent uptake of LDL-derived cholesterol are the major cellular events contributing to fatty streak formation. Many lines of evidence suggest that oxidative or non-oxidative modifications in the lipid and apolipoprotein B (apo B) components of LDL drive the initial formation of fatty streaks (NAVAB et al., *Arterioscler. Thromb. Vasc. Biol.*, vol. 16, p: 831-842, 1996). The specific properties of oxidized LDL (oxLDL), usually studied following oxidation of native LDL in vitro, depend on the extent of modification. This can range from "minimal" modification (mmLDL) wherein the LDL particle can still be recognized by LDL receptors, to extensive oxidation wherein the apoB component is fragmented and lysine residues are covalently modified with reactive breakdown products of oxidized lipids. Such particles are not bound by the LDL receptor but rather by so-called scavenger receptors expressed on macrophages and smooth muscle cells. A large number of proinflammatory and proatherogenic properties have been ascribed to mmLDL and oxLDL and their components. For instance, lysophosphatidylcholine or oxidized phospholipids increase monocyte's adhesion, monocyte and T cell chemotaxis and can induce proinflammatory gene expression. Although the recruitment of monocytes to the arterial wall and their subsequent differentiation into macrophages may initially serve a function by removing cytotoxic and proinflammatory oxLDL particles or apoptotic cells, progressive accumulation of macrophages and their uptake of oxLDL ultimately leads to development of atherosclerotic lesions.

As used herein, the term "T cells" includes lymphocytes which express phenotypic markers and rearrangements of the TCRβ locus with or without rearrangements of the TCRα. Phenotypic markers include expression of CD4 and/or CD8.

The transition from the relatively simple fatty streak to the more complex plaque is characterized by the migration of smooth muscle cells from the medial layer of the artery wall to the internal elastic lamina and to intimal or subendothelial space, or by recruitment of smooth muscle cell progenitors. Intimal smooth muscle cells may proliferate and take up modified lipoproteins, thus contributing to foam cell formation, and synthesize extracellular matrix proteins that lead to the development of the fibrous cap (ROSS, 1999, aforementioned; PAULSSON et al., *Arterioscler. Thromb. Vasc. Biol.*, vol. 20, p: 10-17, 2000). Thus, the advanced atherosclerotic plaque is schematically divided into two portions: the fibrous cap making up the surface layer and a lipid core making up the deep layer. This extra-cellular matrix (ECM) is composed of vastly different macromolecules including collagen, elastin, glycoproteins and proteoglycans (KATSUDA and KAJI, *J. Atheroscler. Thromb.*, vol. 10(5), p: 267-274, 2003). Large amounts of ECM are deposited in the fibrous cap, with the strength of the plaque maintained, whereas in the lipid core in addition to lipid deposition, ECM degradation is enhanced, leading to increased tissue fragility. This plaque fragility gives rise to plaque vulnerability in turn becoming a cause of plaque rupture.

This phase of plaque development is influenced by interactions between monocyte/macrophages and T cells that result in a broad range of cellular and humoral responses and the acquisition of many features of a chronic inflammatory state. Significant cross talk appears to occur among the cellular elements of developing lesions. Lesional T cells appear to be activated and express both Th1 and Th2 cytokines (HANSSON et al., *Circ. Res.*, vol. 91(1), p: 281-91, 2002). Similarly, macrophages, endothelial cells and smooth muscle cells appear to be activated based on their expression of MHC class II molecules and numerous inflammatory products such as TNF, IL-6 and MCP 1.

Most of the T cells in atherosclerotic lesions are CD3+ CD4+ T-cell receptor (TCR) αβ+ cells (JONASSON et al., *Arteriosclerosis*, vol. 6, p: 131-138, 1986; STEMME et al., *Arterioscler. Thromb.*, vol. 12, p: 206-211, 1992). This implies that they recognize protein antigens presented to them by macrophages after uptake and processing through the endosomal pathway. Most of them are of the T-helper (Th1) subtype) which secretes IFN-γ, IL-2, TNFα and -β, and which causes macrophage activation, vascular activation and inflammation (FROSTEGARD et al., *Atherosclerosis*, vol. 145, p: 33-43, 1999). For instance, IFN-γ induces expression of inflammatory cytokines and of secretory phopsholipase A2 which can lead to the production of inflammatory lipid mediators such as eicosanoids, lysophosphatidylcholine and platelet activating factor (PAF). At least three important stimuli for Th1 differentiation are present in the atherosclerotic plaque. The cytokine IL-12 and IL-18 which are produced by many lesion cells is an important stimulus for Th1 differentiation, and both have been shown to promote plaque progression and instability (UYEMURA et al., *J. Clin. Invest.*, vol. 97, p: 2130-8, 1996; MALLAT et al., *Circ. Res.*, vol. 89, p: e41-e45, 2001). Osteopontin, also called early T-lymphocyte activation protein-1 (Eta-1), is needed for Th1 responses and promotes IL-12 expression and granuloma formation (ASHKAR et al., *Science*, vol. 287, p: 860-4, 2000). It is expressed by macrophages, endothelial cells and smooth muscle cells in plaques (O'BRIEN et al., *Arterioscler. Thromb.*, vol. 14, p: 1648-54, 1994) and may be important for local immunity as well as for mineralization. Th2 cytokines such as IL-4, IL-5 and IL-10 are less abundant than cytokines of the Th1 type in end-stage human lesions (FROSTERGARD et al., 1999, aforementioned). Deficiency in IL-4, the prototypic Th2-related cytokine, has been associated with a decrease in atherosclerotic lesion formation, thus suggesting a pro-atherogenic role of Th2, and exaggerated Th2 responses promoted atherosclerotic plaque progression (KING et al., *Arterioscler. Thromb. Vasc. Biol.*, vol. 22, p: 456-461, 2002) as well as aneurysm formation (SHIMIZU et al., *J. Clin. Invest.*, vol. 114, p: 300-308, 2004). Mice showing up-regulation of both Th1 and Th2 responses display enhanced plaque inflammation (GOJOVA et al., *Blood, vol.* 102, p: 4052-4058, 2003; ROBERTSON et al., J. Clin. Invest., vol. 112:1342-1350, 2003). Therefore, even though atherosclerosis occurs mostly in a Th1-related pathogenic context, no direct and solid evidence is available suggesting that promotion of Th2 responses would invariably lead to limitation of disease progression. Moreover, frequent association in humans between atherosclerosis, a Th1-predominant disease, and aortic aneurysm, a Th2-predominant process, suggests a deregulation in both Th1- and Th2-mediated responses (MALLAT and TEDGUI, *Expert. Opin. Biol. Ther.*, vol. 4, p: 1387-1393, 2004).

As used herein, "Th1 cells" refer to a subset of CD4+ T that produces IL-2, IFNγ and lymphotoxin (LT also called TNFβ). Th1 differentiation from naïve T cell is favoured by the presence of exogenous IFNγ, IL-12 and IL-18. The expression of the IL-12R β2 subunit and IL-18r may be considered as a marker for Th1 cells. Th1 play important roles in cellular immune functions such as delayed-type hypersensitivity or in the defense against intracellular organisms such as parasites.

As used herein, "Th2 cells" refer to another subset of cells that produce IL-4, IL-5, IL-6, IL-9, IL-10 and IL-13, but not IL-12 and IFNγ. The essential cytokine for the development of Th2 cells is IL-4. Th2 cells generally enhance antibody production from B cells.

An existing approach for the treatment of atherosclerosis result from the identification of circulating auto-antibodies against oxidized LDL in humans (PALINSKI et al., *Proc. Natl. Acad. Sci. USA*., vol. 86(4), p: 1372-6, 1989) and from the observation that an immunization with oxidized LDL had a effect reducing atherosclerosis with about 50%. In this approach the athero-effect is mediated by antibodies generated against peptidic sequences present in oxLDL. It has been supposed that these antibodies could facilitate the removal of oxLDL by macrophage. Thus, the application WO 02/080954 describes the identification of epitopes in apolipoprotein B that give rise to "antibody formation" in man and the use of efficient quantities of such epitopes in order to induce an humoral immune response corresponding to the production of antibodies.

Another approach is based on evidence that the Th1 and Th2 pathways appear to play a key role. Thus immunomodulatory treatment that promotes regulatory immunity can represent an attractive tool for treating and/or preventing atherosclerosis. This might be accomplished by promoting regulatory T cell generation such as Tr1 cells, CD4+CD25+ cells or Th3 cells. In that context, IL-10 and TGFβ appears to be two of the most interesting cytokines, which are capable of downregulating the inflammatory process triggered by Th1 cells. Indeed IL-10 is a pleiotropic cytokine that is expressed in human atherosclerotic plaques and is mainly produced by macrophages, T helper (Th) type 2 and T regulatory type-1 lymphocytes (Tr1 cells). It has been shown that ex vivo repeated stimulation of naïve T cells with ovalbumin (OVA) and IL-10 results in the generation of T cells clones with immunosuppressives properties, which can prevent in vivo Th1 response after cells injection (GROUX et al., *Nature*, vol. 389(6652), p: 737-42, 1997). On the basis of these observations, a recent study has shown that intraperitoneal administration of OVA-Tr1 cells (expanded in vitro) with their cognate antigen to female apo-E null mice results in a significant reduction of atherosclerotic plaque size (MALLAT et al., *Circulation*, vol. 108(10), p: 1232-7, 2003). Nevertheless, all of these methods actually implicate the administration of the T regulatory cells in the atherosclerotic subjects. Thus, these methods are far to be simple and reliable because they first involve the isolation of T cell from the subject, the stimulation of said T cells with antigen and IL-10 in order to induce regulatory T cells, the expansion of said regulatory T cells and finally the administration of said cells to the subject.

So, there is a recognized and permanent need in the art for new reliable method for triggering a regulatory immune response in order to enhance IL-10 and/or TGFβ to dampen the inflammatory response in atherosclerotic lesions.

The purpose of the present invention is to fulfil this need by providing a composition for generating a specific regulatory immune response, preferably regulatory T cell response, within the atherosclerotic lesion sites to prevent the unwanted Th1/Th2 pro-atherogenic immunity.

Unexpectedly, the inventors have demonstrated that prolonged subcutaneous administration to apoE-null mice of apo B-100 peptides, with a concentration which does not induce an humoral response corresponding to the production of antibodies, by means of ALZET mini pumps, results in the induction of a Treg response which is responsible of plaque antigen specific tolerance.

WO 02/080954 describes a treatment of atherosclerosis by the injection of one or more epitopes derived from apoB-100 in a dose efficient for the induction of specific antibodies' expression. Thus, WO 02/080954 does not describe nor suggest a treatment of atherosclerosis with a "continuous" administration without induction of an humoral response corresponding to the production of specific antibodies. By this way, the present invention limits the risk of inflammatory complications associated with the induction of antibodies' expression.

In one aspect the present invention relates to a method of prophylactic or therapeutic treatment of a subject suffering from atherosclerosis comprising the step of administrating a composition comprising at least one epitope derived from a protein present in the atherosclerotic plaque to said subject with a continuous subcutaneous or transcutaneous administration.

As used herein, the term "subject" denotes a Mammal, such as a rodent, a feline, a canine and a primate. The subject is an animal such as cow, pig, horse, chicken, cat, dog and most preferably a human.

Inflammatory and thrombotic processes are major determinants of atherosclerotic plaque complications leading to acute coronary syndrome (ACS) and sudden death. In addition to pathological studies showing an important association between plaque inflammation and plaque rupture in humans, and experimental data showing a critical role of the immunoinflammatory response both in plaque development and composition, the last decade has witnessed an increasing interest in the study of the role of the systemic inflammatory markers and their relation to the severe complications of atherosclerosis. Several circulating inflammatory markers, including CRP, IL-6, IL-1 receptor antagonist (IL-1ra), vascular cell adhesion molecule (VCAM)-1, and more recently myeloperoxidase, have been shown to be elevated in patients with ACS and to be associated with adverse clinical outcomes at follow-up. Since the landmark study of LIUZZO et al. (*N. Engl. J. Med.*, vol. 331(7), p: 417-24, 1994), numerous studies have addressed the prognostic value of CRP in patients with ACS. Higher CRP levels were associated with increased risk at follow-up in several randomized trials of patients with unstable angina or NSTEMI, including TIMI IIa (MORROW et al., *J. Am. Coll. Cardiol.*, vol 31(7), p: 1460-5, 1998), CAPTURE (HEESCHEN et al., *J. Am. Coll. Cardiol.*, vol 35(6), p: 1535-42, 2000), FRISC (LINDAHL et al., *N. Engl. J. Med.*, vol. 343(16), p: 1139-47, 2000) and GUSTO-IV (JAMES et al., *Circulation*, vol. 108(3), p; 275-81, 2003). CRP levels in ACS patients assigned to early invasive revascularization procedures also predict adverse outcomes (MUELLER, *Circulation*, vol. 105(12), p: 1412-1415, 2002). On the basis of previous experimental data by the inventors and others showing a potent pro-atherogenic role for endogenous IL-18 (MALLAT et al., *Circulation*, vol. 104(4), p: 1598-603, 2001; MALLAT et al., *Circulation Res.*, vol. 89(7), E41-5, 2001; WHITMAN et al., *Circulation Res.*, vol. 90(2), E34-8, 2002), plasma levels have been measured in patients with a history of coronary artery disease and in healthy middle-aged men and was found to be an independent predictor of coronary events (BLANKENBERG et al., *Circulation*, vol. 107(12), p: 1579-85, 2003; BLANKENBERG et al., *Circulation*, vol. 108(20), p: 2453-9, 2003).

The method according to the present invention can be supplied to a subject, which has been diagnosed as presenting one of the following coronary disorders:
asymptomatic coronary artery coronary diseases with silent ischemia or without ischemia;
chronic ischemic disorders without myocardial necrosis, such as stable or effort angina pectoris;
acute ischemic disorders myocardial necrosis, such as unstable angina pectoris;
ischemic disorders with myocardial necrosis, such as ST segment elevation myocardial infarction or non-ST segment elevation myocardial infarction.

Tissue ischemia occurs when the needs in oxygen exceed the delivery of oxygen to tissues. Myocardial ischemia can be diagnosed clinically (e.g. chest pain), biologically (e.g. increase in myeloperoxidase activity), metabolically, using scintigraphy, or by use of an electrocardiogram (typical modifications of the ST segment, upper or lower ST segment deviation, typical changes in T waves such as T wave inversion or steep asymmetric or high amplitude positives T waves). Silent ischemia is typically diagnosed using scintigraphy or a 24 h electrocardiogram recording.

Chronic stable angina results from fixed stenoses in epicardial coronary arteries, which do not limit blood flow at rest, may become flow-limiting during periods of increased myocardial oxygen demand. Stenoses producing a 50% reduction in diameter, or a 70% reduction in cross-sectional area, are sufficient to impair the hyperaemic response that occurs with increasing cardiac work. Selective coronary arteriography is the gold standard for detecting such lesions, although it may underestimate the severity of CAD in more diffusely diseased arteries. Angina pectoris is classically described as a retrosternal pressure that may radiate to the jaw, back, or left arm or shoulder. It may be associated with nausea, diaphoresis and a sense of impending doom. Stable angina is typically brought on by physical exertion, emotional stress, food and exposure to cold. Angina was originally studied in men, and the presentation of angina in women and the elderly tends to be less straightforward. Provocative stress testing with physical or pharmacological stress attempts to induce myocardial ischaemia in a controlled setting. The ischaemic zone may be detected as an electrically abnormal area on electrocardiography (ECG), an area of impaired radionuclide intake with single photon emission computed tomography (SPECT), or as a wall motion abnormality on echocardiography. Patients with typical angina have a high pretest probability of CAD, but a negative test does not exclude the diagnosis.

Unstable angina is defined as new-onset angina, angina at rest, angina of increasing frequency and severity, or angina in the early post-MI setting. The pathological correlate of unstable angina is rupture of an atherosclerotic plaque with formation of a flow-limiting, but nonocclusive, intracoronary platelet-rich thrombus. Vulnerable plaques are thought to have a thick lipid core with a thin fibrous cap and a preponderance of inflammatory cells. The ability to identify which plaques are unstable is limited. Intravascular ultrasonography and intracoronary catheters that can detect temperature differences in plaques are two methods under investigation. Unstable angina and non Q-wave myocardial infarction (NQWMI) are diagnosed by history, examination, ECG and laboratory studies. As noted above, rest pain is the hallmark of unstable angina. The ECG may show ST segment depression in the area of ischaemia, caused by abnormalities of polarization in the ischaemic tissue. The lack of pathologic Q waves on ECG signifies that the infarction is nontransmural. Prolonged ischaemia results in myocardial necrosis and release of the cardiac specific molecule troponin and creatine kinase (CK-MB) into the bloodstream. These markers of necrosis define the presence of MI and are usually evident only in retrospect. Therefore, unstable angina and NQWMI are usually grouped together for purposes of initial management.

Acute myocardial infarction is also known as Q-wave MI, transmural MI, or ST-elevation. It may occur suddenly or be preceded by unstable angina. The pathological correlate of acute MI is rupture of an atherosclerotic plaque with occlusive fibrin and platelet-rich intracoronary thrombus. Complete occlusion of the vessel results in transmural myocardial injury. The clinical presentation of patients with acute MI is protean, ranging from mild chest pain to cardiogenic shock or sudden cardiac death. Physical examination may reveal only abnormal heart sounds or may demonstrate hypotension and pulmonary oedema. The ECG reveals ST-segment elevation in the area of ischaemia representing myocardial injury, and Q waves in areas of infarction. CK-MB and troponin levels are increased. Clinical features that predict a poor outcome include advanced patient age, tachycardia, low blood pressure, and the presence of pulmonary oedema and impaired tissue perfusion.

Preferably, the continuous administration of said composition is carried out for a period of time and at a daily dose of said at least one epitope, which are sufficient to induce a specific regulatory immune response, preferably a Treg response.

As used herein, a specific regulatory immune response is a cellular immune response corresponding to an induction of tolerance for the administrated epitope, which is also present in the atherosclerotic plaque, which can also dampen the immune response against any other epitope present in the micro-environment of the specific epitope by the so called bystander regulatory immune response and inhibit the local inflammatory response, through the release of IL-10 and of TGF-β.

As used herein, a "Treg response" corresponds to a response specific of "Treg cells" or "Tr cells" which refer to a distinct subset of T cells. Tr cells exhibit a cytokine pattern distinct from Th1 and Th2 cells. In particular, Tr cells secrete high amount of IL-10 and subsequent of TGF-β. Tr cells play a major role in induction of tolerance, largely by their ability to suppress responses mediated by other populations of T cells, especially Th1 cells. Tr cells include Tr1 cells and Th3 cells, which are characterized by the secretion of high amount of TGF-β. Tr1 cells secrete high levels of IL-10 and/or TGF-β, with or without IL-5 or IL-13, but little or no IL-2. There exists another subset of Tr cell that is antigen specific and can induce tolerance: CD4+CD25+ T cells. CD4+CD25+ T cells comprise 5-10% of the peripheral T cell pool and exhibit immunosuppressive abilities both in vitro and in vivo. Specifically, CD4+CD25+ T cells express the Foxp3 gene. This regulatory activity may depend on TGFβ or cell-cell contact. Other Th1- or Th2-like cells may exert regulatory activity. As used herein, "Treg response" may be preceded or associated by the induction of tolerogenic antigen presenting cell response.

Advantageously, said continuous administration of said composition is carried out for a period of time within the range of 7 days to 30 days, preferably of 10 days to 20, most preferably about 14 days. This period might be repeated one or several times.

Advantageously, said continuous administration of said composition corresponds to a daily dose within the range of 0.05 to 5000 µg per kg body weight per day, preferably of 0.5 to 1000 µg and more preferably of 5 to 500 µg. This daily dose is sufficient to induce a regulatory immune response but insufficient to induce a humoral immune response corresponding to the production of antibodies, specifically of protective antibodies generated against said epitope, said protective antibodies can for example facilitate the removal of oxidatively damaged LDL particles by macrophages receptor when the used epitope is a peptide derived from apolipoprotein B.

Proteins present in the atherosclerotic plaque are well known from one of skills in the art. Such proteins can include apolipoprotein B-100 (apoB-100, human, Accession number P04114), collagen type I (human, Accession number CAA67261; AAB59577), type III (human, Accession number P02458), type IV (human, Accession number P02462) and type V (human, Accession number CAI17260), elastin (human, Accession number P15502), laminin (human, Accession number P024043; Q16363), entactin/nidogen (human, Accession number P14543), fibronectin (human, Accession number NP_997647; NP_997643; NP_997641; NP_997640; NP_997639; NP_997635), thrombospondin (human, Accession number NP_003237), vitronectin (human, Accession number P04004), tenascin (human, Accession number P24821), osteopontin (human, Accession number NP_000573), proteoglycans [glycorin, decorin (human, Accession number AAV38603), versican, hyaluronan], medin (human, Accession number Q08431), lactadherin (human, Accession number Q08431), β-amyloid (human, Accession number P05067), HSP 60 (human, Accession number AAA36022.1) or HSP 70 (human, Accession number BAA24847.1). Preferably, the protein is selected among apoB-100, HSP 60 and HSP 70, most preferably the protein is apoB-100.

Epitopes from these proteins can be simply identified by one of skills in the art. These epitopes correspond to proteins present in the atherosclerotic plaque or to synthetic peptides from more than 10 amino acids length, more preferably from more than 15 amino acids, derived from such a protein and which can be presented in a MHC class II context. Such epitopes corresponding to proteins present in the atherosclerotic plaque can be obtained by grinding an atherosclerotic plaque as described in XU et al. (*Arterioscler Thromb*. Vol. 12(7), p: 789-799, 1992).

Preferably, theses epitopes correspond to synthetic peptides. Typically, the length of these peptides is comprised between 15 and 25 amino acids. Such epitopes can include the apoB-100 epitopes described in WO 02/080954, the HSP 60 and HSP 70 epitopes described in WYSOCKI et al. (*Cardiovasc. Pathol*. vol. 11, p: 238-243, 2002) and in CHAN et al. (*Eur. J. Vasc. Endovasc. Surg*. Vol. 18, p: 381-385, 1999).

For the epitopes derived from apoB-100, the peptides can be used in their native state, or after incorporation in phopholipid liposomes, after a modification of the amino acids that mimics the different modifications of apoB-100 protein that may occur during oxidation or non-oxidative modification of LDL. Preferably, this modification is selected among oxidation by exposure to copper, oxidation after aldehyde-modification, like malone dealdehyde (MDA), hydroxynonenal or other aldehydes, or acetylation, most preferably this modification corresponds to oxidation after malone dealdehyde (MDA)-modification.

Preferably, these epitopes correspond to the peptides below:

| | |
|---|---|
| FLDTVYGNCSTHFTVKTRKG; | (SEQ ID NO: 1) |
| PQCSTHILQWLKRVHANPLL; | (SEQ ID NO: 2) |
| VISIPRLQAEARSEILAHWS; | (SEQ ID NO: 3) |
| KLVKEALKESQLPTVMDFRK; | (SEQ ID NO: 4) |
| LFVTQAEGAKQTEATMTFK; | (SEQ ID NO: 5) |
| DGSLRHKFLDSNIKFSHVEK; | (SEQ ID NO: 6) |
| KGTYGLSCQRDPNTGRLNGE; | (SEQ ID NO: 7) |
| RLNGESNLRFNSSYLQGTNQ; | (SEQ ID NO: 8) |
| SLTSTSDLQSGIIKNTASLK; | (SEQ ID NO: 9) |
| TASLKYENYELTLKSDTNGK; | (SEQ ID NO: 10) |
| DMTSFKQNALLRSEYQADYE; | (SEQ ID NO: 11) |
| MKVKIIRTIDQMQNSELQWP; | (SEQ ID NO: 12) |
| IALDDAKINFNEKLSQLQTY; | (SEQ ID NO: 13) |
| KTTKQSFDLSVKAQYKKNKH; | (SEQ ID NO: 14) |
| EEEMLENVSLVCPKDATRFK; | (SEQ ID NO: 15) |
| GSTSHHLVSRKSISAALEHK; | (SEQ ID NO: 16) |
| IENIDFNKSGSSTASWIQNV; | (SEQ ID NO: 17) |
| IREVTQRLNGEIQALELPQK; | (SEQ ID NO: 18) |
| EVDVLTKYSQPEDSLIPFFE; | (SEQ ID NO: 19) |
| HTFLIYITELLKKLQSTTVM; | (SEQ ID NO: 20) |
| LLDIANYLMEQIQDDCTGDE; | (SEQ ID NO: 21) |
| CTGDEDYTYKIKRVIGNMGQ; | (SEQ ID NO: 22) |
| GNMGQTMEQLTPELKSSILK; | (SEQ ID NO: 23) |
| SSILKCVQSTKPSLMIQKAA; | (SEQ ID NO: 24) |
| IQKAAIQALRKMEPKDKDQE; | (SEQ ID NO: 25) |
| RLNGESNLRFNSSYLQGTNQ; | (SEQ ID NO: 26) |
| SLNSHGLELNADILGTDKIN; | (SEQ ID NO: 27) |
| WIQNVDTKYQIRIQIQEKLQ; | (SEQ ID NO: 28) |
| TYISDWWTLAAKNLTDFAEQ; | (SEQ ID NO: 29) |
| EATLQRIYSLWEHSTKNHLQ; | (SEQ ID NO: 30) |
| ALLVPPETEEAKQVLFLDTV; | (SEQ ID NO: 31) |
| IEIGLEGKGFEPTLEALFGF; | (SEQ ID NO: 32) |
| SGASMKLTTNGRFREHNAKF; | (SEQ ID NO: 33) |
| NLIGDFEVAEKINAFRAKVH; | (SEQ ID NO: 34) |
| GHSVLTAKGMALFGEGKAEF; | (SEQ ID NO: 35) |
| FKSSVITLNTNAELFNQSDI; | (SEQ ID NO: 36) |
| FPDLGQEVALNANTKNQKIR; | (SEQ ID NO: 37) |
| ATRFKHLRKYTYNYQAQSSS. | (SEQ ID NO: 38) |

More preferably, the peptides are selected among IALD-DAKINFNEKLSQLQTY (SEQ ID NO: 13), and KTTKQS-FDLSVKAQYKKNKH (SEQ ID NO: 14).

Advantageously, said at least on epitope is not administrated with any adjuvant or any effective amount of such an adjuvant likely to induce antibodies' expression.

In another aspect the present invention relates to a kit adapted for the prophylactic or therapeutic treatment of a subject suffering from atherosclerosis comprising:
(i) a composition comprising an effective amount of at least one epitope derived from a protein present in the atherosclerotic plaque; and
(ii) means for administrating subcutaneously or transcutaneously said composition in a continuous manner, whereby said continuous administration to a subject induces a specific regulatory immune response, preferably a Treg response.

Means for administrating subcutaneously or transcutaneously a composition in a continuous manner are well known of one of skill in the art. Such means include needle with pump.

Said means enable an administration of said composition for a period of time within the range of 7 days to 30 days, preferably of 10 days to 20, most preferably about 14 days. This period might be repeated one or several times.

Moreover, said means enable a continuous administration of said composition corresponding to a daily dose within the range of 0.05 to 5000 µg per kg body weight per day, preferably of 0.5 to 1000 µg and more preferably of 5 to 500 µg.

Advantageously, the composition of said kit does not contain any adjuvant or any effective amount of such an adjuvant likely to induce antibodies' expression. Such adjuvants are well known from one of skills in the art (e.g. DNA with non methylated CG nucleotides).

The composition of the kit according to the present invention can be supplied to a subject, which has been diagnosed as presenting one of the following coronary disorders:
asymptomatic coronary artery coronary diseases with silent ischemia or without ischemia;
chronic ischemic disorders without myocardial necrosis, such as stable or effort angina pectoris;
acute ischemic disorders myocardial necrosis, such as unstable angina pectoris;
ischemic disorders with myocardial necrosis, such as ST segment elevation myocardial infarction or non-ST segment elevation myocardial infarction.

Advantageously, said composition comprises at least one epitope derived from a protein present in the atherosclerotic plaque in an amount within the range of 0.05 µg to 250 mg per milliliter, preferably of 0.5 µg to 50 mg per milliliter and more preferably of 5 µg to 25 mg.

Proteins present in the atherosclerotic plaque are well known from one of skills in the art. Such proteins can include apolipoprotein B-100 (apoB-100, human, Accession number P04114), collagen type I (human, Accession number CAA67261; AAB59577), type III (human, Accession number P02458), type IV (human, Accession number P02462) and type V (human, Accession number CAI17260), elastin (human, Accession number P15502), laminin (human, Accession number P024043; Q16363), entactin/nidogen (human, Accession number P14543), fibronectin (human, Accession number NP_997647; NP_997643; NP_997641; NP_997640; NP_997639; NP_997635), thrombospondin (human, Accession number NP_003237), vitronectin (human, Accession number P04004), tenascin (human, Accession number P24821), osteopontin (human, Accession number NP_000573), proteoglycans [glycorin, decorin (human, Accession number AAV38603), versican, hyaluronan], medin (human, Accession number Q08431), lactadherin (human, Accession number Q08431), β-amyloid (human, Accession number P05067), HSP 60 (human, Accession number AAA36022.1) or HSP 70 (human, Accession number BAA24847.1). Preferably, the protein is selected among apoB-100, HSP 60 and HSP 70, most preferably the protein is apoB-100.

Epitopes from these proteins can be simply identified by one of skills in the art. These epitopes correspond to proteins present in the atherosclerotic plaque or to synthetic peptides from more than 10 amino acids length, more preferably from more than 15 amino acids, derived from such a protein and which can be presented in a MHC class II context. Such epitopes corresponding to proteins present in the atherosclerotic plaque can be obtained by grinding an atherosclerotic plaque as described in XU et al. (1992, abovementioned).

Preferably, these epitopes correspond to synthetic peptides. Typically, the length of these peptides is comprised between 15 and 25 amino acids. Such epitopes can include the apoB-100 epitopes described in WO 02/080954, the HSP 60 and HSP 70 epitopes described in WYSOCKI et al. (2002, abovementioned) and in CHAN et al. (1999, abovementioned).

For the epitopes derived from apoB-100, the peptides can be used in their native state, or after incorporation in phopholipid liposomes, after a modification of the amino acids that mimics the different modifications of apoB-100 protein that may occur during oxidation or non-oxidative modification of LDL. Preferably, this modification is selected among oxidation by exposure to copper, oxidation after aldehyde-modification, like malone dealdehyde (MDA), hydroxynonenal or other aldehydes, or acetylation, most preferably this modification corresponds to oxidation after malone dealdehyde (MDA)-modification.

Preferably, these epitopes correspond to the peptides below:

```
FLDTVYGNCSTHFTVKTRKG;      (SEQ ID NO: 1)
PQCSTHILQWLKRVHANPLL;      (SEQ ID NO: 2)
VISIPRLQAEARSEILAHWS;      (SEQ ID NO: 3)
KLVKEALKESQLPTVMDFRK;      (SEQ ID NO: 4)
LFVTQAEGAKQTEATMTFK;       (SEQ ID NO: 5)
DGSLRHKFLDSNIKFSHVEK;      (SEQ ID NO: 6)
KGTYGLSCQRDPNTGRLNGE;      (SEQ ID NO: 7)
RLNGESNLRFNSSYLQGTNQ;      (SEQ ID NO: 8)
SLTSTSDLQSGIIKNTASLK;      (SEQ ID NO: 9)
TASLKYENYELTLKSDTNGK;      (SEQ ID NO: 10)
DMTSFKQNALLRSEYQADYE;      (SEQ ID NO: 11)
MKVKIIRTIDQMQNSELQWP;      (SEQ ID NO: 12)
IALDDAKINFNEKLSQLQTY;      (SEQ ID NO: 13)
KTTKQSFDLSVKAQYKKNKH;      (SEQ ID NO: 14)
EEEMLENVSLVCPKDATRFK;      (SEQ ID NO: 15)
GSTSHHLVSRKSISAALEHK;      (SEQ ID NO: 16)
IENIDFNKSGSSTASWIQNV;      (SEQ ID NO: 17)
IREVTQRLNGEIQALELPQK;      (SEQ ID NO: 18)
EVDVLTKYSQPEDSLIPFFE;      (SEQ ID NO: 19)
HTFLIYITELLKKLQSTTVM;      (SEQ ID NO: 20)
LLDIANYLMEQIQDDCTGDE;      (SEQ ID NO: 21)
CTGDEDYTYKIKRVIGNMGQ;      (SEQ ID NO: 22)
GNMGQTMEQLTPELKSSILK;      (SEQ ID NO: 23)
SSILKCVQSTKPSLMIQKAA;      (SEQ ID NO: 24)
IQKAAIQALRKMEPKDKDQE;      (SEQ ID NO: 25)
RLNGESNLRFNSSYLQGTNQ;      (SEQ ID NO: 26)
SLNSHGLELNADILGTDKIN;      (SEQ ID NO: 27)
WIQNVDTKYQIRIQIQEKLQ;      (SEQ ID NO: 28)
TYISDWWTLAAKNLTDFAEQ;      (SEQ ID NO: 29)
EATLQRIYSLWEHSTKNHLQ;      (SEQ ID NO: 30)
ALLVPPETEEAKQVLFLDTV;      (SEQ ID NO: 31)
IEIGLEGKGFEPTLEALFGF;      (SEQ ID NO: 32)
SGASMKLTTNGRFREHNAKF;      (SEQ ID NO: 33)
NLIGDFEVAEKINAFRAKVH;      (SEQ ID NO: 34)
GHSVLTAKGMALFGEGKAEF;      (SEQ ID NO: 35)
FKSSVITLNTNAELFNQSDI;      (SEQ ID NO: 36)
FPDLGQEVALNANTKNQKIR;      (SEQ ID NO: 37)
ATRFKHLRKYTYNYQAQSSS.      (SEQ ID NO: 38)
```

More preferably, the peptides are selected among IALDDAKINFNEKLSQLQTY (SEQ ID NO: 13), and KTTKQSFDLSVKAQYKKNKH (SEQ ID NO: 14).

The composition may comprise a vehicle. For example, the composition may comprise emulsions, microemulsions, oil-in-water emulsions, anhydrous lipids and oil-in-water emulsions, other types of emulsions. The composition may also comprise one or more additives (e.g., diluents, excipients, stabilizers, preservatives). See, generally, *Ullmann's Encyclopedia of Industrial Chemistry*, 6th Ed. (various editors, 1989-1998, Marcel Dekker); and *Pharmaceutical Dosage Forms and Drug Delivery Systems* (ANSEL et al., 1994, WILLIAMS & WILKINS).

Epitope may be solubilized in a buffer or water or incorporated in emulsions and microemulsions. Suitable buffers include, but are not limited to, phosphate buffered saline $Ca^{++}/Mg^{++}$ free (PBS), phosphate buffered saline (PBS), normal saline (150 mM NaCl in water), and Tris buffer.

There are numerous causes of peptide instability or degradation, including hydrolysis and denaturation. Hydrophobic interaction may cause clumping of molecules together (i.e. aggregation). This result may entail diminution of the induction of a Treg response. Stabilizers may be added to lessen or prevent such problems.

Stabilizers include cyclodextrine and derivatives thereof (see U.S. Pat. No. 5,730,969). Suitable preservatives such as sucrose, mannitol, sorbitol, trehalose, dextran and glycerin can also be added to stabilize the final formulation. A stabilizer selected from non-ionic surfactants, D-glucose, D-galactose, D-xylose, D-galacturonic acid, trehalose, dextrans, hydroxyethyl starches, and mixtures thereof may be added to the formulation. Addition of alkali metal salt or magnesium chloride may stabilize a peptide. The peptide may also be stabilized by contacting it with a saccharide selected from the group consisting of dextran, chondroitin sulphuric acid, starch, glycogen, dextrin, and alginic acid salt. Other sugars that can be added include monosaccharides, disaccharides, sugar alcohols, and mixtures thereof (E.g., glucose, mannose, galactose, fructose, sucrose, maltose, lactose, mannitol, xylitol). Polyols may stabilize a peptide, and are water-miscible or water-soluble. Suitable polyols may be polyhydroxy alcohols, monosaccharides and disaccharides including mannitol, glycrol, ethylene glycol, propylene glycol, trimethyl glycol, vinyl pyrrolidone, glucose, fructose, arabinose, mannose, maltose, sucrose, and polymers thereof. Various excipients may also stabilize peptides, including serum albumin, amino acids, heparin, fatty acids and phospholipids, surfactants, metals, polyols, reducing agents, metal chelating agents, polyvinyl pyrrolidone, hydrolysed gelatin, and ammonium sulfate.

In another aspect the invention relates to a patch adapted for the prophylactic or therapeutic treatment by continuous transcutaneous administration of a subject, suffering from atherosclerosis, said patch comprising:
(a) a dressing, and
(b) an effective amount of at least one epitope derived from a protein present in the atherosclerotic plaque,
whereby application of said patch to intact skin induces a specific regulatory immune response, preferably a Treg response.

The production of such a patch is described in US patent application 2004/0028727 A1 in the name of Gregory M. GLENN.

The patch according to the present invention can be applied to a subject, which has been diagnosed as presenting one of the following coronary disorders:
asymptomatic coronary artery coronary diseases with silent ischemia or without ischemia;
chronic ischemic disorders without myocardial necrosis, such as stable or effort angina pectoris;
acute ischemic disorders myocardial necrosis, such as unstable angina pectoris;
ischemic disorders with myocardial necrosis, such as ST segment elevation myocardial infarction or non-ST segment elevation myocardial infarction.

The dressing may be occlusive or non-occlusive.

Advantageously, said effective amount of at least one epitope is adapted for obtaining an administration of a daily dose of said at least one epitope within the range of 0.05 to 5000 µg per kg body weight per day, preferably of 0.5 to 1000 µg and more preferably of 5 to 500 µg. This daily dose is sufficient to induce a regulatory immune response but insufficient to induce an humoral immune response corresponding to the production of antibodies, specifically of protective antibodies generated against said epitope, which could for example facilitate the removal of oxidatively damaged LDL particles by macrophages receptor when the used epitope is a peptide derived from apolipoprotein B.

For effective treatment, multiples patches may be applied at frequent intervals or constantly over a period of time within the range of 7 days to 30 days, preferably of 10 days to 20, most preferably about 14 days. (see U.S. Pat. No. 5,049,387 and Example 1 for a detailed description of a patch); or may be applied simultaneously.

Proteins present in the atherosclerotic plaque are well known from one of skills in the art. Such proteins can include apolipoprotein B-100 (apoB-100, human, Accession number P04114), collagen type I (human, Accession number CAA67261; AAB59577), type III (human, Accession number P02458), type IV (human, Accession number P02462) and type V (human, Accession number CAI17260), elastin (human, Accession number P15502), laminin (human, Accession number P024043; Q16363), entactin/nidogen (human, Accession number P14543), fibronectin (human, Accession number NP_997647; NP_997643; NP_997641; NP_997640; NP_997639; NP_997635), thrombospondin (human, Accession number NP_003237), vitronectin (human, Accession number P04004), tenascin (human, Accession number P24821), osteopontin (human, Accession number NP_000573), proteoglycans [glycorin, decorin (human, Accession number AAV38603), versican, hyaluronan], medin (human, Accession number Q08431), lactadherin (human, Accession number Q08431), β-amyloid (human, Accession number P05067), HSP 60 (human, Accession number AAA36022.1) or HSP 70 (human, Accession number BAA24847.1). Preferably, the protein is selected among apoB-100, HSP 60 and HSP 70, most preferably the protein is apoB-100.

Epitopes from these proteins can be simply identified by one of skills in the art. These epitopes correspond to proteins present in the atherosclerotic plaque or to synthetic peptides from more than 10 amino acids length, more preferably from more than 15 amino acids, derived from such a protein and which can be presented in a MHC class II context. Such epitopes corresponding to proteins present in the atherosclerotic plaque can be obtained by grinding an atherosclerotic plaque as described in XU et al. (1992, abovementioned).

Preferably, these epitopes correspond to synthetic peptides. Typically, the length of these peptides is comprised between 15 and 25 amino acids. Such epitopes can include the apoB-100 epitopes described in WO 02/080954, the HSP 60 and HSP 70 epitopes described in WYSOCKI et al. (2002, abovementioned) and in CHAN et al. (1999, abovementioned).

For the epitopes derived from apoB-100, the peptides can be used in their native state, or after incorporation in phopholipid liposomes, after a modification of the amino acids that mimics the different modifications of apoB-100 protein that may occur during oxidation or non-oxidative modification of LDL. Preferably, this modification is selected among oxidation by exposure to copper, oxidation after aldehyde-modification, like malone dealdehyde (MDA), hydroxynonenal or other aldehydes, or acetylation, most preferably this modification corresponds to oxidation after malone dealdehyde (MDA)-modification.

Preferably, these epitopes correspond to the peptides below:

```
FLDTVYGNCSTHFTVKTRKG;     (SEQ ID NO: 1)

PQCSTHILQWLKRVHANPLL;     (SEQ ID NO: 2)

VISIPRLQAEARSEILAHWS;     (SEQ ID NO: 3)

KLVKEALKESQLPTVMDFRK;     (SEQ ID NO: 4)

LFVTQAEGAKQTEATMTFK;      (SEQ ID NO: 5)

DGSLRHKFLDSNIKFSHVEK;     (SEQ ID NO: 6)

KGTYGLSCQRDPNTGRLNGE;     (SEQ ID NO: 7)

RLNGESNLRFNSSYLQGTNQ;     (SEQ ID NO: 8)

SLTSTSDLQSGIIKNTASLK;     (SEQ ID NO: 9)

TASLKYENYELTLKSDTNGK;     (SEQ ID NO: 10)
```

-continued

| | |
|---|---|
| DMTSFKQNALLRSEYQADYE; | (SEQ ID NO: 11) |
| MKVKIIRTIDQMQNSELQWP; | (SEQ ID NO: 12) |
| IALDDAKINFNEKLSQLQTY; | (SEQ ID NO: 13) |
| KTTKQSFDLSVKAQYKKNKH; | (SEQ ID NO: 14) |
| EEEMLENVSLVCPKDATRFK; | (SEQ ID NO: 15) |
| GSTSHHLVSRKSISAALEHK; | (SEQ ID NO: 16) |
| IENIDFNKSGSSTASWIQNV; | (SEQ ID NO: 17) |
| IREVTQRLNGEIQALELPQK; | (SEQ ID NO: 18) |
| EVDVLTKYSQPEDSLIPFFE; | (SEQ ID NO: 19) |
| HTFLIYITELLKKLQSTTVM; | (SEQ ID NO: 20) |
| LLDIANYLMEQIQDDCTGDE; | (SEQ ID NO: 21) |
| CTGDEDYTYKIKRVIGNMGQ; | (SEQ ID NO: 22) |
| GNMGQTMEQLTPELKSSILK; | (SEQ ID NO: 23) |
| SSILKCVQSTKPSLMIQKAA; | (SEQ ID NO: 24) |
| IQKAAIQALRKMEPKDKDQE; | (SEQ ID NO: 25) |
| RLNGESNLRFNSSYLQGTNQ; | (SEQ ID NO: 26) |
| SLNSHGLELNADILGTDKIN; | (SEQ ID NO: 27) |
| WIQNVDTKYQIRIQIQEKLQ; | (SEQ ID NO: 28) |
| TYISDWWTLAAKNLTDFAEQ; | (SEQ ID NO: 29) |
| EATLQRIYSLWEHSTKNHLQ; | (SEQ ID NO: 30) |
| ALLVPPETEEAKQVLFLDTV; | (SEQ ID NO: 31) |
| IEIGLEGKGFEPTLEALFGF; | (SEQ ID NO: 32) |
| SGASMKLTTNGRFREHNAKF; | (SEQ ID NO: 33) |
| NLIGDFEVAEKINAFRAKVH; | (SEQ ID NO: 34) |
| GHSVLTAKGMALFGEGKAEF; | (SEQ ID NO: 35) |
| FKSSVITLNTNAELFNQSDI; | (SEQ ID NO: 36) |
| FPDLGQEVALNANTKNQKIR; | (SEQ ID NO: 37) |
| ATRFKHLRKYTYNYQAQSSS. | (SEQ ID NO: 38) |

More preferably, the peptides are selected among IALD-DAKINFNEKLSQLQTY (SEQ ID NO: 13), and KTTKQS-FDLSVKAQYKKNKH (SEQ ID NO: 14).

The patch may include a controlled, released reservoir or, a matrix or rate controlling membrane, which allows stepped release of epitope. Such a patch is described in EP 0318385. Preferably said epitope is maintained in a dry form prior to administration. Subsequent release of liquid from a reservoir or entry of liquid into the reservoir containing the dry ingredient of the formulation will at least partially dissolve that ingredient.

The formulation may comprise a vehicle. For example, the formulation may comprise AQUAFOR (an emulsion of petrolatum, mineral oil, mineral wax, wool wax, panthenol, bisabol, and glycerin as shown in WO 98/20734), emulsions, microemulsions, gels, oil-in-water emulsions, anhydrous lipids and oil-in-water emulsions, other types of emulsions, fats waxes, oil, silicones, gels and humectants. The formulation may also comprise one or more additives (e.g., diluents, binders, excipients, stabilizers, dessicants, preservatives, coloring). See, generally, *Ullmann's Encyclopedia of Industrial Chemistry*, (abovementioned) and *Pharmaceutical Dosage Forms and Drug Delivery Systems* (abovementioned).

Advantageously, said formulation does not contain any adjuvant or any effective amount of such an adjuvant likely to induce antibodies' expression.

Epitope may be solubilized in a buffer or water or organic solvents such as alcohol or DMSO, or incorporated in gels, emulsions, microemulsions, and creams. Suitable buffers include, but are not limited to, phosphate buffered saline $Ca^{++}/Mg^{++}$ free (PBS), phosphate buffered saline (PBS), normal saline (150 mM NaCl in water), and Tris buffer. Epitope not soluble in neutral buffer can be solubilized in 10 mM acetic acid and then diluted to the desired volume with a neutral buffer such as PBS. In the case of epitope soluble only at acid pH, acetate-PBS at acid pH may be used as a diluent after solubilization in dilute acetic acid. Glycerol may be a suitable non-aqueous buffer for use in the invention.

There are numerous causes of peptide instability or degradation, including hydrolysis and denaturation. Hydrophobic interaction may cause clumping of molecules together (i.e. aggregation). This result may entail diminution of the induction of a Treg response. Stabilizers may be added to lessen or prevent such problems.

This formulation, or any intermediate in its production, may be pretreated with agents (i.e., cryoprotectants and dry stabilizers) and then subjected to cooling rates and final temperatures that minimize ice crystal formation. By proper selection of cryo agents and use of pre-selected drying parameters, almost any formulation might be cryoprepared for a suitable desired end use.

Stabilizers include cyclodextrine and derivatives thereof (see U.S. Pat. No. 5,730,969). Suitable preservatives such as sucrose, mannitol, sorbitol, trehalose, dextran and glycerin can also be added to stabilize the final formulation. A stabilizer selected from non-ionic surfactants, D-glucose, D-galactose, D-xylose, D-galacturonic acid, trehalose, dextrans, hydroxyethyl starches, and mixtures thereof may be added to the formulation. Addition of alkali metal salt or magnesium chloride may stabilize a peptide. The peptide may also be stabilized by contacting it with a saccharide selected from the group consisting of dextran, chondroitin sulphuric acid, starch, glycogen, dextrin, and alginic acid salt. Other sugars that can be added include monosaccharides, disaccharides, sugar alcohols, and mixtures thereof (E.g., glucose, mannose, galactose, fructose, sucrose, maltose, lactose, mannitol, xylitol). Polyols may stabilize a peptide, and are water-miscible or water-soluble. Suitable polyols may be polyhydroxy alcohols, monosaccharides and disaccharides including mannitol, glycrol, ethylene glycol, propylene glycol, trimethyl glycol, vinyl pyrrolidone, glucose, fructose, arabinose, mannose, maltose, sucrose, and polymers thereof. Various excipients may also stabilize peptides, including serum albumin, amino acids, heparin, fatty acids and phospholipids, surfactants, metals, polyols, reducing agents, metal chelating agents, polyvinyl pyrrolidone, hydrolysed gelatin, and ammonium sulfate.

In another aspect the present invention relates to the Use of at least one epitope derived from a protein present in the atherosclerotic plaque for the manufacture of a medicament for use in the prevention or treatment by continuous subcutaneous or transcutaneous administration, which induce a specific regulatory immune response, preferably a Treg response, to a subject suffering from atherosclerosis.

Said medicament can be administrated to a subject, which has been diagnosed as presenting one of the following coronary disorders:

asymptomatic coronary artery coronary diseases with silent ischemia or without ischemia;

chronic ischemic disorders without myocardial necrosis, such as stable or effort angina pectoris;

acute ischemic disorders myocardial necrosis, such as unstable angina pectoris;

ischemic disorders with myocardial necrosis, such as ST segment elevation myocardial infarction or non-ST segment elevation myocardial infarction.

Preferably, said medicament is administrated for a period of time and at a daily dose of said at least one epitope, which are sufficient to induce a regulatory immune response, preferably a Treg response.

Proteins present in the atherosclerotic plaque are well known from one of skills in the art. Such proteins can include apolipoprotein B-100 (apoB-100, human, Accession number P04114), collagen type I (human, Accession number CAA67261; AAB59577), type III (human, Accession number P02458), type IV (human, Accession number P02462) and type V (human, Accession number CAI17260), elastin (human, Accession number P15502), laminin (human, Accession number P024043; Q16363), entactin/nidogen (human, Accession number P14543), fibronectin (human, Accession number NP_997647; NP_997643; NP_997641; NP_997640; NP_997639; NP_997635), thrombospondin (human, Accession number NP_003237), vitronectin (human, Accession number P04004), tenascin (human, Accession number P24821), osteopontin (human, Accession number NP_000573), proteoglycans [glycorin, decorin (human, Accession number AAV38603), versican, hyaluronan], medin (human, Accession number Q08431), lactadherin (human, Accession number Q08431), β-amyloid (human, Accession number P05067), HSP 60 (human, Accession number AAA36022.1) or HSP 70 (human, Accession number BAA24847.1). Preferably, the protein is selected among apoB-100, HSP 60 and HSP 70, most preferably the protein is apoB-100.

Epitopes from these proteins can be simply identified by one of skills in the art. These epitopes correspond to proteins present in the atherosclerotic plaque or to synthetic peptides from more than 10 amino acids length, more preferably from more than 15 amino acids, derived from such a protein and which can be presented in a MHC class II context. Such epitopes corresponding to proteins present in the atherosclerotic plaque can be obtained by grinding an atherosclerotic plaque as described in XU et al. (2002, abovementioned).

Preferably, these epitopes correspond to synthetic peptides. Typically, the length of these peptides is comprised between 15 and 25 amino acids. Such epitopes can include the apoB-100 epitopes described in WO 02/080954, the HSP 60 and HSP 70 epitopes described in WYSOCKI et al. (2002, abovementioned) and in CHAN et al. (1999, abovementioned).

For the epitopes derived from apoB-100, the peptides can be used in their native state, or after incorporation in phopholipid liposomes, after a modification of the amino acids that mimics the different modifications of apoB-100 protein that may occur during oxidation or non-oxidative modification of LDL. Preferably, this modification is selected among oxidation by exposure to copper, oxidation after aldehyde-modification, like malone dealdehyde (MDA), hydroxynonenal or other aldehydes, or acetylation, most preferably this modification corresponds to oxidation after malone dealdehyde (MDA)-modification.

Preferably, these epitopes correspond to the peptides below:

| | |
|---|---|
| FLDTVYGNCSTHFTVKTRKG; | (SEQ ID NO: 1) |
| PQCSTHILQWLKRVHANPLL; | (SEQ ID NO: 2) |
| VISIPRLQAEARSEILAHWS; | (SEQ ID NO: 3) |
| KLVKEALKESQLPTVMDFRK; | (SEQ ID NO: 4) |
| LFVTQAEGAKQTEATMTFK; | (SEQ ID NO: 5) |
| DGSLRHKFLDSNIKFSHVEK; | (SEQ ID NO: 6) |
| KGTYGLSCQRDPNTGRLNGE; | (SEQ ID NO: 7) |
| RLNGESNLRFNSSYLQGTNQ; | (SEQ ID NO: 8) |
| SLTSTSDLQSGIIKNTASLK; | (SEQ ID NO: 9) |
| TASLKYENYELTLKSDTNGK; | (SEQ ID NO: 10) |
| DMTSFKQNALLRSEYQADYE; | (SEQ ID NO: 11) |
| MKVKIIRTIDQMQNSELQWP; | (SEQ ID NO: 12) |
| IALDDAKINFNEKLSQLQTY; | (SEQ ID NO: 13) |
| KTTKQSFDLSVKAQYKKNKH; | (SEQ ID NO: 14) |
| EEEMLENVSLVCPKDATRFK; | (SEQ ID NO: 15) |
| GSTSHHLVSRKSISAALEHK; | (SEQ ID NO: 16) |
| IENIDFNKSGSSTASWIQNV; | (SEQ ID NO: 17) |
| IREVTQRLNGEIQALELPQK; | (SEQ ID NO: 18) |
| EVDVLTKYSQPEDSLIPFFE; | (SEQ ID NO: 19) |
| HTFLIYITELLKKLQSTTVM; | (SEQ ID NO: 20) |
| LLDIANYLMEQIQDDCTGDE; | (SEQ ID NO: 21) |
| CTGDEDYTYKIKRVIGNMGQ; | (SEQ ID NO: 22) |
| GNMGQTMEQLTPELKSSILK; | (SEQ ID NO: 23) |
| SSILKCVQSTKPSLMIQKAA; | (SEQ ID NO: 24) |
| IQKAAIQALRKMEPKDKDQE; | (SEQ ID NO: 25) |
| RLNGESNLRFNSSYLQGTNQ; | (SEQ ID NO: 26) |
| SLNSHGLELNADILGTDKIN; | (SEQ ID NO: 27) |
| WIQNVDTKYQIRIQIQEKLQ; | (SEQ ID NO: 28) |
| TYISDWWTLAAKNLTDFAEQ; | (SEQ ID NO: 29) |
| EATLQRIYSLWEHSTKNHLQ; | (SEQ ID NO: 30) |
| ALLVPPETEEAKQVLFLDTV; | (SEQ ID NO: 31) |
| IEIGLEGKGFEPTLEALFGF; | (SEQ ID NO: 32) |
| SGASMKLTTNGRFREHNAKF; | (SEQ ID NO: 33) |
| NLIGDFEVAEKINAFRAKVH; | (SEQ ID NO: 34) |
| GHSVLTAKGMALFGEGKAEF; | (SEQ ID NO: 35) |
| FKSSVITLNTNAELFNQSDI; | (SEQ ID NO: 36) |
| FPDLGQEVALNANTKNQKIR; | (SEQ ID NO: 37) |
| ATRFKHLRKYTYNYQAQSSS. | (SEQ ID NO: 38) |

More preferably, the peptides are selected among IALD-DAKINFNEKLSQLQTY (SEQ ID NO: 13), and KTTKQS-FDLSVKAQYKKNKH (SEQ ID NO: 14).

Advantageously, said medicament does not contain any adjuvant or any effective amount of such an adjuvant likely to induce antibodies' expression.

Advantageously, said medicament is administrated for a period of time within the range of 7 days to 30 days, preferably of 10 days to 20, most preferably about 14 days. This period might be repeated one or several times.

Advantageously, said medicament is administrated at a daily dose within the range of 0.05 to 5000 µg per kg body weight per day, preferably of 0.5 to 1000 µg and more preferably of 5 to 500 µg. This daily dose is sufficient to induce a regulatory immune response but insufficient to induce an humoral immune response corresponding to the production of antibodies, specifically of protective antibodies generated against said epitope, which could for example facilitate the removal of oxidatively damaged LDL particles by macrophages receptor when the used epitope is a peptide derived from apolipoprotein B.

The invention is further illustrated below by the following Examples, which are not intended to limit its scope.

EXAMPLE 1

1. Peptides

P210: Human apoB-100 derived peptide (SEQ ID NO: 14, KTTKQSFDLSVKAQYKKNKH, amino acids 3136 to 3155). The homology between human (Accession number: P04114) and mouse (Accession number: XP_137955) sequences is 90% for this peptide.

MDA P210: Malondialdehyde (MDA)-modified human apoB-100 derived peptide. A fraction of native P210 was modified by 0.5 mol/L MDA for 3 hours at 37° C. The MDA-modified peptide was dialysed against PBS containing 1 mmol/L EDTA with several changes for 18 hours at 4° C. The MDA modification of P210 was assessed using the thiobarbituric acid reactive substances assay.

P240: Human apoB-100 derived peptide (SEQ ID NO: 37, FPDLGQEVALNANTKNQKIR, amino acids 3586 to 3605). The homology between human (Accession number: P04114) and mouse (Accession number: XP_137955) sequences is 86% amino acids 3591 to 3604 (SEQ ID NO: 39, QEVAL-NANTKNQKI).

Control: phosphate buffer saline (PBS).

2. Peptide Delivery Pump Treatment

Male ApoE −/− mice (B&M, RY, DENMARK, 11 week old) were implanted subcutaneously with mini-osmotic pumps (ALZET1002, DURECT CORPORATION) diffusing PBS or 10 µg of P210, MDA-P210 or P240 per day and for 14 day, at a rate of 0.25 µl/h.

Then, the mice are kept for another 6 weeks and killed at 19 weeks of age.

3. Purification and Culture of Spleen and Lymph Node Cells

T cells were purified from spleen or from draining lymph nodes by negative selection with anti-CD11b (M1/70), anti B220, anti-CD8 and anti-NK cells (DX5) followed by depletion with a mixture of magnetic beads coated with anti-rat Ig (DYNAL). CD11c+ dendritic cells were purified by positive selection with anti-CD11c using directly conjugated anti-CD11c beads (clone N418; MILTENYI BIOTEC).

For cytokine measurements, purified T cells were cultured in 96-well plates in the presence of anti-CD3 (5 µg/ml) and anti-CD28 (1 µg/ml) antibodies. Supernatants were collected at 24 hours (for IL-4 measurements) and at 48 hours (for IL-5, IL-10 and IFN-γ measurements) and assayed for cytokine levels by ELISA.

For the cell proliferation assay, purified CD4+ cells (50 000) were mixed with CD11c+ cells (10 000) and anti-CD3 antibodies (3 µg/ml) for 72 hours. [3H]-Thymidine (1 µCi; PERKIN ELMER) was added for the last 18 hours of cell culture.

Co-culture experiments were performed to evaluate regulatory T cell function. Isolated dendritic cells were also assessed for their cytokine production 4. Analysis of Atherosclerotic Plaque Size and Composition Total Plasma and HDL cholesterol were measured with a commercially available cholesterol kit (SIGMA) according to the manufacturer's instructions. Morphometric and immuno-histochemical studies were performed in the aortic sinus and in the thoracic aorta (spanning from the brachiocephalic artery to the renal arteries). Collagen fibers were stained with Sirius red. Immuno-histochemical analysis were then performed. The following primary antibodies were used: MOMA-2 (BIOSOURCE INTERNATIONAL) as a specific marker for macrophages; anti-mouse CD3− (SANTA CRUZ); anti-smooth muscle actin, alkaline phosphatase conjugate, clone 1A4 (SIGMA); and anti-IL-10 antibody (SANTA CRUZ). Morphometric analysis was performed with an automated image processor (HISTOLAB, MICROVISION).

5. Determination of Antibody Titers Against Peptide

Native or MDA-modified peptides 210 and 240 were used for coating (10 µg/ml of each in PBS pH 7.4) microtiter plates (Nunc MaxiSorp, Nunc, Roskilde, Denmark) in an overnight incubation at 4° C. Coated plates were washed with PBS with 0.05% Tween-20 and thereafter blocked with SuperBlock in Tris-buffered saline (TBS, Pierce) for 5 minutes at room temperature followed by an incubation of mouse serum diluted 1:50 in TBS-0.05% Tween-20 for 2 hours at room temperature and overnight at 4° C. After rinsing, depositions were detected by using biotinylated goat anti-mouse IgM or IgG antibodies (JACKSON IMMUNORESEARCH, West Grove, Pa.) that were incubated for 2 hours at room temperature. The plates were washed and bound biotinylated antibodies were detected by alkaline phosphatase-conjugated streptavidin (SIGMA). The color reaction was developed using phosphatase substrate kit (Pierce). The absorbency at 405 nm was measured after 1 hour of incubation at room temperature. Mean values were calculated after subtraction of background absorbance.

6. Determination of Functional Regulatory T Cell Activity

CD4+CD25− cells in RPMI 1640 supplemented with Glutamax, 10% FCS, 0.02 mM 2β-mercaptoethanol and antibiotics were co-cultured with CD11c+ dendritic cells and CD4+CD25+ regulatory T cells at a ratio of CD25−/CD25+ of 1:1, 1:2, 1:4, 1:8, in flat-bottomed 96-well microplates ($0.5 \times 10^5$ cells/well; total volume 200 µl/well). Cells were stimulated with purified soluble CD3-specific antibody (1 µg/ml, Pharmingen). Cells were cultured at 37° C. for 72 h and pulsed with 1 µCi of [$^3$H] thymidine (Amersham) for the last 18 h of culture. Thymidine incorporation was assessed using a TopCount NXT scintillation counter (Perkin Elmer).

7. Results

Total plasma cholesterol levels were not different in the different groups: 4.82±0.60 g/l in control mice receiving PBS, 5.84±0.61 g/l in mice receiving MDA-P210, 4.66±0.45 g/l in mice receiving P210, and 4.95±0.59 g/l in mice receiving P240.

Lesion size in the control group receiving PBS was 80 664±14 541 µm$^2$. It was markedly reduced in mice receiving MDA-P210 (26 479±4 303 µm$^2$, p<0.0007) and P210 (32 301±11 307 µm$^2$, p<0.003), and less, albeit significantly, decreased in mice receiving P240 (41 688±10 301 µm$^2$, p<0.02).

Proliferation of CD4+ cells from control mice in the presence of CD11c+ cells from mice receiving MDA-P210 was markedly decreased compared with that in the presence of CD11c+ cells from control mice receiving PBS (9500 cpm versus 20 000 cpm), indicating that dendritic cells from mice receiving MDA-P210 acquired tolerogenic potential.

IgG antibody levels against native or MDA-modified peptides were not significantly different in the different groups. IgG against P210 were 0.81±0.22, 0.51±0.07, 0.47±0.09 and 0.94±0.72 absorbance units in P210, MDA-P210, P240 and PBS groups, respectively. IgG against MDA-P210 were 1.45±0.49, 0.83±0.28, 0.62±0.11 and 0.82±0.42 absorbance units in P210, MDA-P210, P240 and PBS groups, respectively. IgG against P240 were undectable. IgG against MDA-P240 were 0.080±0.038, 0.041±0.007, 0.037±0.007 and 0.049±0.019 absorbance units in P210, MDA-P210, P240 and PBS groups, respectively.

IgM antibody levels against native or MDA-modified peptides were not significantly different in the different groups. IgM against P210 were 1.17±0.22, 0.55±0.25, 0.79±0.45 and 1.05±0.30 absorbance units in P210, MDA-P210, P240 and PBS groups, respectively. IgM against MDA-P210 were 1.38±0.04, 1.30±0.13, 0.79±0.45 and 1.39±0.08 absorbance units in P210, MDA-P210, P240 and PBS groups, respectively. IgM against P240 were undectable. IgM against MDA-P240 were 1.80±0.41, 1.24±0.40, 1.34±0.52 and 1.14±0.62 absorbance units in P210, MDA-P210, P240 and PBS groups, respectively.

EXAMPLE 2

1. Peptides

P210: Human apoB-100 derived peptide (SEQ ID NO: 14, KTTKQSFDLSVKAQYKKNKH, amino acids 3136 to 3155). The homology between human (Accession number: P04114) and mouse (Accession number: XP_137955) sequences is 90% for this peptide.

MDA P210: Malondialdehyde (MDA)-modified human apoB-100 derived peptide. A fraction of native P210 was modified by 0.5 mol/L MDA for 3 hours at 37° C. The MDA-modified peptide was dialysed against PBS containing 1 mmol/L EDTA with several changes for 18 hours at 4° C. The MDA modification of P210 was assessed using the thiobarbituric acid reactive substances assay.

P240: Human apoB-100 peptide (SEQ ID NO: 37, FPDLGQEVALNANTKNQKIR, amino acids 3586 to 3605). The homology between human (Accession number: P04114) and mouse (Accession number: XP_137955) sequences is 86% between amino acids 3591 and 3604 (SEQ ID NO: 39, QEVALNANTKNQKI).

Control: chicken ovalbumin (OVA) peptide (SEQ ID NO: 40, ISQAVHAAHAEINEAGR, amino acids 323 to 339).

2. Peptide Delivery Pump Treatment

Male apoE−/− mice (B&M, RY, DENMARK, 11 week old) were implanted subcutaneously with mini-osmotic pumps (ALZET1002, DURECT CORPORATION) diffusing phosphate buffer saline (PBS) as control or 10 µg per day of P210, MDA-P210 or P240, for 14 days, at a rate of 0.25 µL/l. An additional group of mice receiving ovalbumin (OVA) peptide (323-339) served as control.

Then, the mice were kept for another 6 or 10 weeks and killed at 19 or 23 weeks of age.

3. Purification and Culture of Spleen and Lymph Node Cells

CD4+ cells were purified from spleen and draining lymph nodes by negative selection with anti-CD11b (M1/70), anti B220, anti CD8 and anti-NK cells (DX5) followed by depletion with a mixture of magnetic beads coated with anti-rat Ig (DYNAL). CD11c+ dendritic cells were purified by positive selection with anti-CD11c using directly conjugated anti-CD11c beads (clone N418; MILTENYI BIOTEC).

For cytokine measurements, purified T cells were cultured in 96-well plates in the presence of anti-CD3 (5 µg/mL)+anti-CD28 (1 µG/mL) antibodies. Supernatants were collected at 24 hours (for IL-4 measurements) and at 48 hours (for IL-5, IL-10 and IFN-γ measurements) and assayed for cytokine levels by ELISA.

For the cell proliferation assay, purified CD4+ cells (50 000) were mixed with CD11c+ dendritic cells (10 000) and anti-CD3 antibodies (3 µg/ml) for 72 hours. [3H]-Thymidine (1 µCi; PERKIN ELMER) was added for the last 18 hours of cell culture.

Co-culture experiments were performed to evaluate regulatory T cell function. Isolated dendritic cells were also assessed for their cytokine production.

4. Analysis of Atherosclerotic Plaque Size and Composition

Total Plasma and HDL cholesterol were measured with a commercially available cholesterol kit (SIGMA) according to the manufacturer's instructions. Morphometric and immuno-histochemical studies were performed in the aortic sinus and in the thoracic aorta (spanning from the brachiocephalic artery to the renal arteries). Collagen fibers were stained with Sirius red. Immuno-histochemical analysis were then performed. The following primary antibodies were used: MOMA-2 (BIOSOURCE INTERNATIONAL) as a specific marker for macrophages; anti-mouse CD3− (SANTA CRUZ); anti-smooth muscle actin, alkaline phosphatase conjugate, clone 1A4 (SIGMA); and anti-IL-10 antibody (SANTA CRUZ). Morphometric analysis was performed with an automated image processor (HISTOLAB, MICROVISION).

5. Results

Male apoE−/− mice (11-week old) were implanted subcutaneously with mini-osmotic pumps (ALZET1002) diffusing phosphate buffer saline (PBS), as control, or 10 µg per day of P210, MDA-P210 or P240, for 14 days at a rate of 0.25 μl/h. An additional group of mice receiving ovalbumin (OVA) peptide (323-339) served as control. Mice were kept for another 6 weeks and killed at 19 weeks of age.

Total plasma cholesterol levels were not different in the different groups: 5.09±0.78 g/L in control mice receiving PBS, 4.94±0.39 g/L in mice receiving P210, 5.49±0.50 g/L in mice receiving MDA-P210, 4.81±0.51 g/L in mice receiving P240, and 5.51±0.78 in mice receiving OVA.

Lesion size in the control group receiving PBS was 67 001±12 194 μm2 (n=9). It was markedly reduced in mice receiving P210 (27 428±7 735 μm2, n=9, p<0.0015), MDA-P210 (31 791±4 284 μm2, n=11, p<0.0029) or P240 (38 080±7 546 μm2, n=8, p<0.02), but was not significantly different in mice receiving OVA (52 720±10 227, n=5, p=0.31).

To evaluate whether the anti-atherogenic effect of subcutaneous administration of low doses of apoB peptides for 14 days persists at long term, male apoE−/− mice (11-week old) were implanted with mini-osmotic pumps diffusing PBS, P210, MDA-P210 or P240 for 14 days were kept for another 10 weeks and killed at 23 weeks of age.

Total plasma cholesterol levels were not different in the different groups: 6.38±0.87 g/L in mice receiving PBS, 5.40±0.67 g/L in mice receiving P210, 4.67±0.89 g/L in mice receiving MDA-P210, 6.64±0.64 g/L in mice receiving P240.

Lesion size in the control group receiving PBS was 96 203±13 498 μm2 (n=6). It was markedly reduced in mice receiving P210 (58 543±16 735 μm2, n=6, p<0.05) or P240 (53 920±8 045 μm2, n=8, p<0.02), but it was not different in mice receiving MDA-P210 (69 026±12 443 μm2, n=4, p=0.19)

The continuous administration of p210 peptide and p210 MDA to apoE null mice results in a diminution of the atherosclerotic plaques and of associated inflammation, together with a change in the composition of the plaque toward a more stable phenotype. No significant modification was observed with the administration of the control peptide.

The invention claimed is:

1. A method for treating atherosclerosis in a subject, which comprises a continuous subcutaneous or transcutaneous administration to said subject of a therapeutically effective amount of at least one epitope for a period of time within the range of 7 to 30 days and at a daily dose within the range of 0.05 to 5000 µg per kg body weight per day, wherein the at least one epitope is administered for a period of time and at a daily dose, which are sufficient to induce a specific regulatory immune response, and wherein said epitope is a synthetic peptide derived from apolipoprotein B-100 (apoB-100), wherein said synthetic peptide is selected from the group consisting of:

KTTKQSFDLSVKAQYKKNKH (SEQ ID NO: 14);

FPDLGQEVALNANTKNQKIR (SEQ ID NO: 37); and

SEQ ID NO: 14 or 37 modified to mimic a modification of apoB-100 protein that may occur during oxidation or non-oxidative modification of LDL, selected from the group consisting of oxidation by exposure to copper, oxidation after aldehyde-modification or acetylation.

2. The method according to claim 1, wherein the subject has been diagnosed as presenting one of the following coronary disorders:

an asymptomatic coronary artery coronary disease with silent ischemia or without ischemia;

a chronic ischemic disorder without myocardial necrosis;

an acute ischemic disorder with myocardial necrosis; and an ischemic disorder with myocardial necrosis.

3. The method according to claim 1, wherein the at least one epitope is administered for a period of time within the range of 10 days to 20 days.

4. The method according to claim 1, wherein the at least one epitope is administered at a daily dose within the range of 0.5 to 1000 µg per kg body weight per day.

5. The method according to claim 2, wherein the chronic ischemic disorder without myocardial necrosis is stable angina pectoris.

6. The method according to claim 2, wherein the acute ischemic disorder with myocardial necrosis is unstable angina pectoris.

7. The method according to claim 2, wherein the ischemic disorder with myocardial necrosis is ST segment elevation myocardial infarction or non-ST segment elevation myocardial infarction.

* * * * *

UNITED STATES PATENT AND TRADEMARK OFFICE
CERTIFICATE OF CORRECTION

PATENT NO. : 8,324,152 B2
APPLICATION NO. : 11/813071
DATED : December 4, 2012
INVENTOR(S) : Alain Tedgui et al.

It is certified that error appears in the above-identified patent and that said Letters Patent is hereby corrected as shown below:

On the title page, please amend Item (73) to read as follows:

-- (73) Assignee: Institut National de la Sante et de la Recherche Medicale (INSERM), Paris (FR) --

Signed and Sealed this
Nineteenth Day of March, 2013

Teresa Stanek Rea
*Acting Director of the United States Patent and Trademark Office*